United States Patent
Darian

(10) Patent No.: US 8,894,673 B2
(45) Date of Patent: Nov. 25, 2014

(54) ULTRASONIC OSTEOTOME

(75) Inventor: Alexander L. Darian, Brightwaters, NY (US)

(73) Assignee: Misonix, Incorporated, Farmingdale, NY (US)

( * ) Notice: Subject to any disclaimer, the term of this patent is extended or adjusted under 35 U.S.C. 154(b) by 0 days.

(21) Appl. No.: 13/268,057

(22) Filed: Oct. 7, 2011

(65) Prior Publication Data
US 2013/0090660 A1    Apr. 11, 2013

(51) Int. Cl.
  *A61B 17/16*  (2006.01)
  *A61B 17/32*  (2006.01)
  *A61B 17/14*  (2006.01)
  *A61B 19/00*  (2006.01)

(52) U.S. Cl.
  CPC .......... *A61B 17/14* (2013.01); *A61B 17/320068* (2013.01); *A61B 2017/320072* (2013.01); *A61B 2019/481* (2013.01)
  USPC ............................................. 606/169; 606/84

(58) Field of Classification Search
  USPC ....................... 606/79, 84, 169; 433/118, 119; D24/144
  See application file for complete search history.

(56) References Cited

U.S. PATENT DOCUMENTS

| | | | | |
|---|---|---|---|---|
| 4,832,683 | A | * | 5/1989 | Idemoto et al. .................. 604/22 |
| 5,135,528 | A | * | 8/1992 | Winston .......................... 606/79 |
| 5,935,143 | A | * | 8/1999 | Hood ............................. 606/169 |
| 2001/0004695 | A1 | | 6/2001 | Vercellotti et al. |
| 2008/0188878 | A1 | | 8/2008 | Young |
| 2009/0143795 | A1 | | 6/2009 | Robertson |
| 2009/0318944 | A1 | | 12/2009 | Kimura et al. |

FOREIGN PATENT DOCUMENTS

KR    10-0884211 B1    2/2009

* cited by examiner

*Primary Examiner* — Christian Sevilla
(74) *Attorney, Agent, or Firm* — R. Neil Sudol; Henry D. Coleman

(57) ABSTRACT

An ultrasonic osteotome in accordance with the present invention comprises a shaft having a distal end portion with a lateral outer surface and further comprises a cutting blade connected to the distal end portion of the shaft at least in part at the lateral outer surface. The lateral outer surface extends so far on opposite sides of the blade as to block or stop penetration of the shaft into an incision formed in bone tissue by the blade. The blade can include a cutting notch or have a variable cutting depth depending on the angle of the distal end of the instrument to the surface of a target tissue mass.

14 Claims, 3 Drawing Sheets

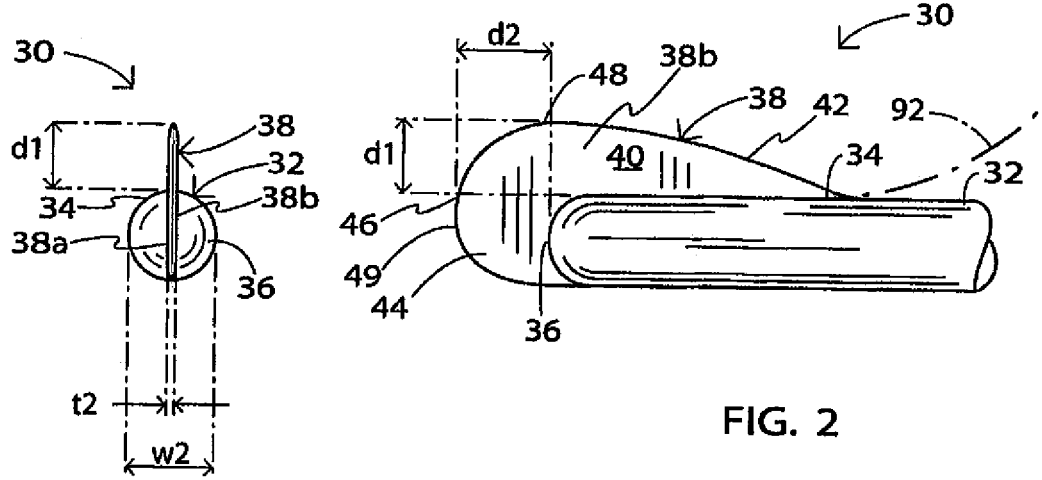
FIG. 1
FIG. 2
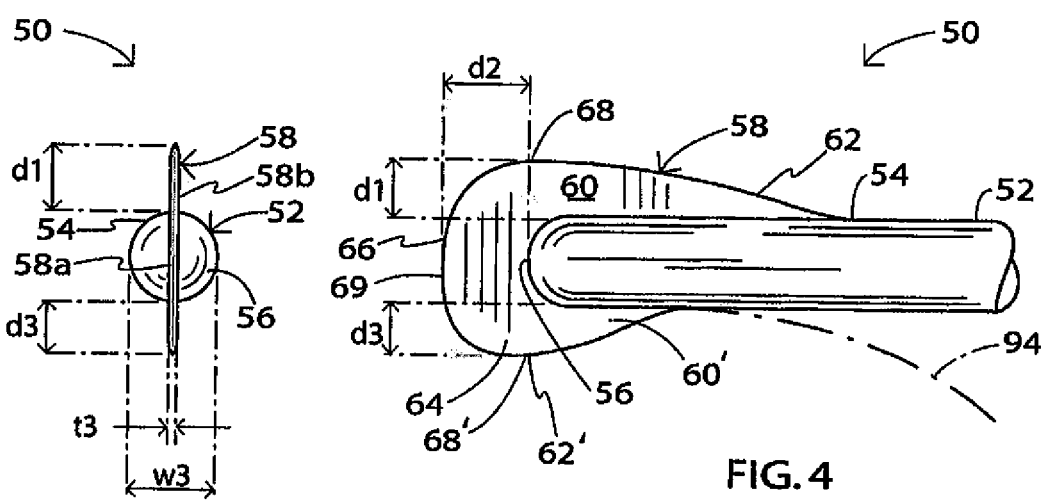
FIG. 3
FIG. 4

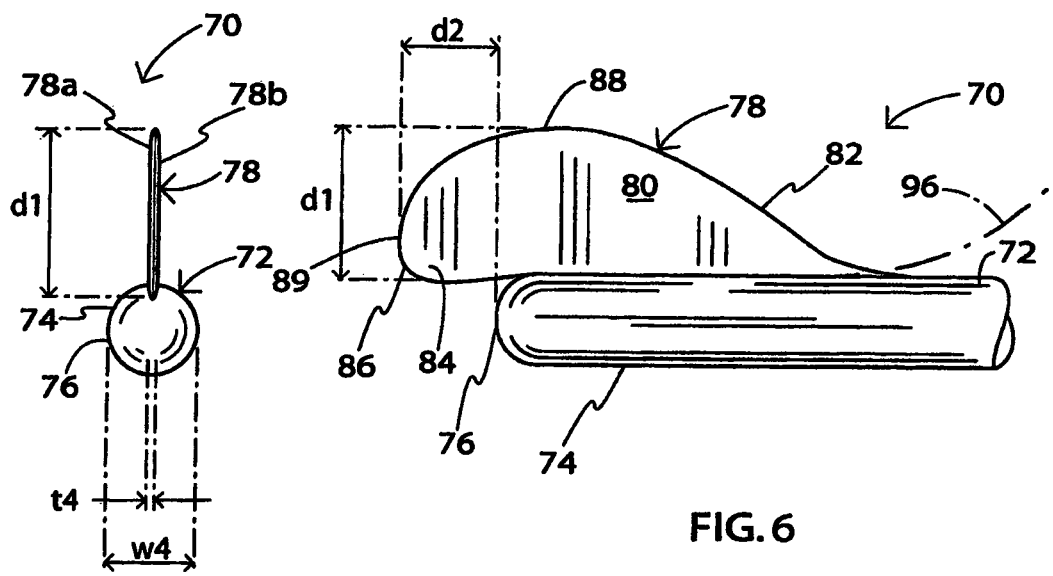
FIG. 5
FIG. 6
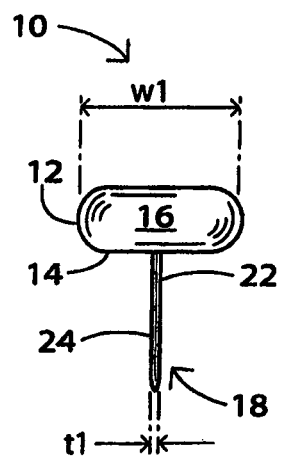
FIG. 7
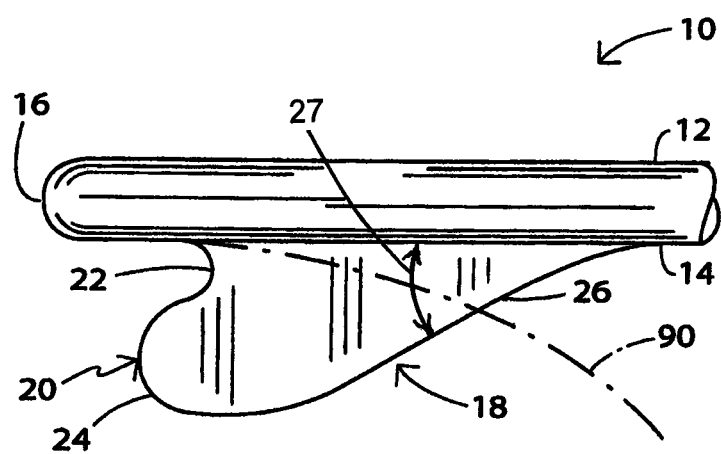
FIG. 8

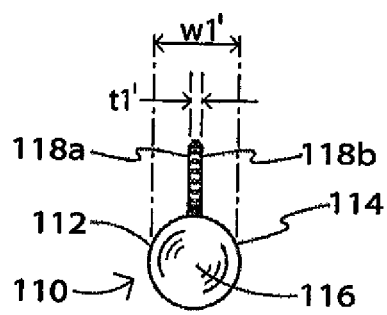
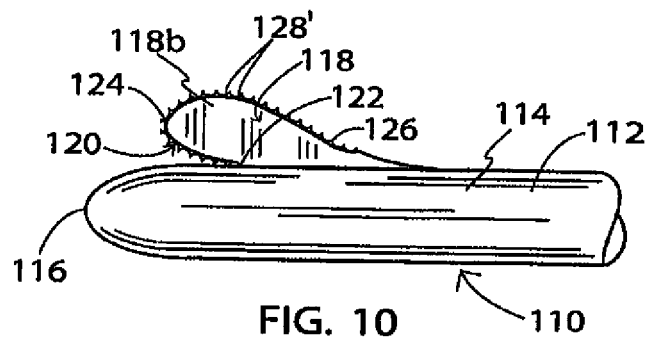
FIG. 9  FIG. 10
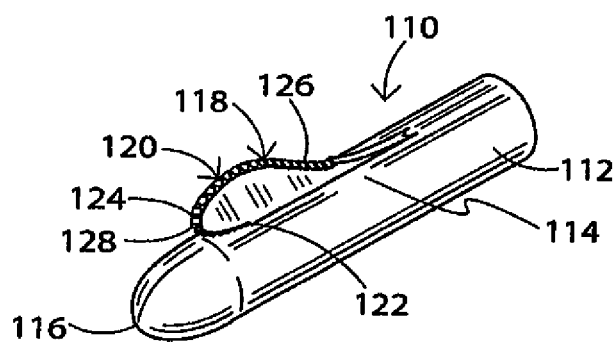
FIG. 11
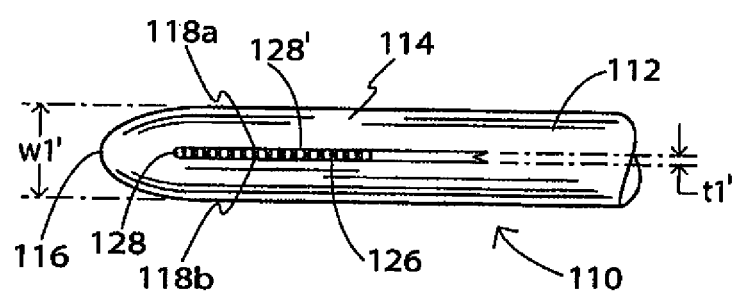
FIG. 12

ULTRASONIC OSTEOTOME

BACKGROUND OF THE INVENTION

This invention also pertains to an ultrasonic surgical blade utilizable for incising bone.

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade which has teeth arranged around its circumference similar to a table saw blade. All of these traditional bone saws are used today in medical procedures around the world.

While traditional saws are functional, they have many disadvantages. With either the band or reciprocating saws, for instance, it is not easy to initiate and direct a cut. A cut must start from an edge or, alternatively, a starting hole must be used. To create a starting hole, a drill or similar instrument is operated to bore into the bone. Subsequently, a cutting blade is inserted into the bored hole. The user can then proceed to cut. Alternatively, a rotary type blade may be used. However, when a rotary blade is used, the cut must follow a relatively straight path to prevent the blade from binding in the cut. With all blades the ability to create a curved or compound angle cut is extremely limited by the blade chosen. The relatively thick blades have a wide kerf; so that a significant thickness of the viable bone is lost in the cutting procedure. Physicians would like this width to be as thin as possible in most procedures where reconstruction is necessary.

Over the past 30 years, several ultrasonic tools have been invented which can be used to ablate or cut tissue in surgery. Wuchinich et al. in U.S. Pat. No. 4,223,676 and Idemoto et al in U.S. Pat. No. 5,188,102 disclose such devices.

Ultrasonic surgical devices generally fall into two categories. One is a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as microstreaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under unwanted tumors to separate it from the surrounding structure. The surgeon can then lift the tissue out using common tools such as forceps.

A second kind of ultrasonic device uses a flat blade instead of a blunt hollow probe. Here a cutting action takes place. Such a flat ultrasonic blade is the subject of U.S. Pat. Nos. 6,379,371 and 6,443,969. As disclosed therein, the blade shape is semicircular at the distal portion with two straight sides parallel to the longitudinal axis and extending back to the shoulder that contacts the vibrating probe. Male threads are shown which mate with the female threaded socket of the probe (or transducer) to allow tight intimate contact of the probe and blade tip shoulder. When the two are torqued together, they form a single resonant body that will vibrate in sympathy with the transducer and generator combination. The distal end of the blade will vibrate with an amplitude set by the mechanical gain of the probe/tip geometry and the input amplitude provided by the transducer generator combination. This motion provided the cutting action for the tissue in question.

The blade of U.S. Pat. Nos. 6,379,371 and 6,443,969 was intended for the cutting or excising of bone or similarly hard tissue in surgical applications. In tests conducted in vitro and in vivo, it was noted that the blade, when sharp, cut both hard and soft tissue with similar ease. In delicate operations, such as sinus lift surgery or craniotomies where the goal is to cut an aperture in the front of the skull to expose sinus tissue or brain but not cut the membrane directly beneath the bony structure, this is very important. It is also important in spinal and brain surgery where bone tissue must be cut with a minimum of damage to underlying soft tissues such as the dura mater. It was noted in early in vitro testing that the blade, as it plunged through the cortex of the bone punctured the membrane or ripped it. After some experience, competent surgeons were able to master the technique, but the learning curve was steep.

In certain applications, such as sinus cavity lifts and maxillofacial surgery such as third molar extraction, a tool would be useful which could cut the harder bony material with less trauma while sparing the soft tissues underneath.

OBJECTS OF THE INVENTION

It is an object of the present invention to provide an improved ultrasonic osteotome.

More particularly, it is an object of the present invention to provide an ultrasonic osteotome that facilitates bone-cutting procedures.

Another even more particular object of the present invention is to provide such an ultrasonic osteotome that reduces the likelihood of damage to soft tissues.

A further object of the present invention is to provide such an ultrasonic osteotome that exhibits increased stability, particularly in view of the magnitudes of force that are necessary.

These and other objects of the present invention will be apparent from the descriptions and drawings herein. Although every object of the invention is attainable by at least one embodiment of the invention, there is not necessarily any single embodiment that achieves all of the objects of the invention.

SUMMARY OF THE INVENTION

An ultrasonic osteotome in accordance with the present invention comprises a shaft having a distal end portion with a lateral outer surface and further comprises a cutting blade connected to the distal end portion of the shaft at least in part at the lateral outer surface. The lateral outer surface extends so far on opposite sides of the blade as to block or stop penetration of the shaft into an incision formed in bone tissue by the blade.

Generally, that portion of the lateral outer surface of the shaft that comes into contact with the target tissue of the patient at a surgical site has a total effective width, measured perpendicularly to the blade, which is at least two times the thickness of the blade. More preferably, the tissue-contacting portion of the lateral outer surface has a width that is about three times the thickness of the blade. It is contemplated that the blade is a thin flat plate, with a thickness on the order of 0.020 inch. Consequently, the tissue-contacting portion of the lateral outer surface has a width that is at least about 0.040 to 0.060 inch wide.

Where the shaft is cylindrical at its distal end, the width of the tissue-contacting portion of the lateral outer surface is a fraction of the shaft diameter, typically between one-third and two-thirds. As described below, the shaft may have a rounded rectangular cross-section, so that the width of the tissue-contacting portion of the lateral outer surface is a larger fraction of the entire shaft width, as measured transversely to the blade.

In one embodiment of the present invention, the blade has an edge formed on at least one side (distal, proximal, or both) with a cutting notch adjacent to the lateral outer surface and a protruding bulge on a side of the notch opposite the lateral outer surface. Preferably, the edge is continuous over or along the notch and the bulge and has an arcuate form. At least along portions of the bulge, the edge must be smooth, that is, free of discontinuities, sharp notches, sharp teeth, or other sharp points that would tend to cut, lacerate, or otherwise damage soft tissue that is disposed adjacent to bone tissue that is being cut with the blade.

That portion of the blade's edge along the notch and the bulge may have an S-shaped configuration.

The notch may be beveled, serrated or toothed. In addition, the protruding portion or bulge may be formed with serrations or teeth (see FIGS. 9-12). However, the serrations or teeth along at least an outer aspect of the bulge must be smoothly configured, without discontinuities or sharp points that would cut, lacerate, or otherwise damage soft tissue.

In this first embodiment of the invention, the blade is disposed on only one side of the distal end portion of the shaft, the shaft extending in a distal direction beyond the blade. Where the blade is formed with only one notch, either on the distal side or the proximal side, the other side of the blade is gently sloped at an acute angle towards the lateral surface of the shaft, so that the blade has the appearance of a sailboat keel.

In another embodiment of the present invention, the blade extends distally beyond a distal tip of the shaft. This embodiment of the osteotome has a blade width, i.e., that dimension of the blade measured between the cutting edge and the outer surface of the shaft, which varies so as to provide the user with multiple choices as to cutting depth.

In variations of this embodiment, the blade includes a distal end portion that is attached to the shaft at the blunt distal tip. Thus, the blade is attached to the shaft along the lateral outer surface thereof, as well as at the blunt distal tip. The blade has a pair of opposed major faces and a maximum thickness measured in a given direction perpendicular to the major faces, the blunt distal tip having a width or breadth measured substantially parallel to the given direction, the width or breadth of the shaft tip being sufficiently greater than the thickness of the blade so as to block or stop penetration of the shaft into an incision formed in bone tissue by the distal end portion of the blade.

Preferably, in this embodiment of the invention, the blade has a proximal blade portion with a proximally facing edge sloped at an acute angle relative to the lateral outer shaft surface at the distal end portion of the shaft. The distal end portion of the blade has a distally facing convex edge. The convex edge and the proximally facing edge are smoothly continuous with one another in a gently or smoothly arcuate curve. This curve may have the profile of a liquid drop, optionally skewed to one side.

Pursuant to another feature of the present invention, where the blade extends distally of the shaft tip, the blade has a first maximum width dimension as measured in a longitudinal direction between the convex blade edge and the blunt distal tip of the shaft. Also, the blade has a second maximum width dimension as measured in a transverse direction between a lateral edge of the blade and the lateral outer surface of the shaft. The first maximum width dimension and the second maximum width dimension may be substantially different from one another for enabling of facilitating variation in a depth of incision made via use of the osteotome.

In a specific embodiment of the invention, the blade may extend from one side of the shaft, over the distal shaft tip, to the opposite side of the shaft. In that case, the blade has a third maximum width dimension as measure in a transverse direction between another lateral edge of the blade and the lateral outer surface of the shaft on a side of the shaft opposite the second maximum width dimension. The third maximum width dimension may be different from both the first maximum width dimension and the second maximum width dimension.

It is contemplated that the blade is centrally disposed relative to the shaft, so that the blade lies in a common plane with the axis of the distal end portion of the shaft. In that event, the blade is disposed in a plane oriented substantially perpendicularly to the lateral outer surface even when the shaft is cylindrical. However, it is possible for the blade to be eccentrically disposed in a plane that is not coaxial with the distal end portion of the shaft, but extends parallel with the axis. In the latter case, the blunt distal tip extends eccentrically on laterally or transversely opposite sides of the distal end portion of the blade.

Pursuant to another feature of the present invention, the shaft and its lateral outer surface are curved to match a curvature of an outer bone surface. Thus, the lateral outer surface of the shaft has an arcuate profile in a longitudinal plane including an axis of the shaft.

As indicated above, the shaft may be cylindrical or have a cross-section that is of another shape, such as rectangular with rounded corners. In the latter instance, the lateral outer surface of the shaft includes a portion at the blade that is at least substantially planar.

An ultrasonic osteotome in accordance with the present invention facilitates bone cutting by preventing the blade from extending through a target bone tissue mass at a surgical site and substantially into soft tissue underlying the target bone. Thus, the ultrasonic osteotome described herein protects soft tissue while enabling a smooth clean incision through overlying bone.

Certain embodiments of the invention provide an adjustability in cutting depth by varying the angle at which the bone cutting blade enters the target tissue. The angle of the distal end portion of the shaft relative to a surface of a target tissue mass is readily observable and is associated with respective incision depths.

BRIEF DESCRIPTION OF THE DRAWINGS

FIG. 1 is a front elevational view of a first embodiment of an ultrasonic osteotome in accordance with the present invention.

FIG. 2 is a side elevational view of the ultrasonic osteotome of FIG. 1.

FIG. 3 is a front elevational view of a second embodiment of an ultrasonic osteotome in accordance with the present invention.

FIG. 4 is a side elevational view of the ultrasonic osteotome of FIG. 3.

FIG. 5 is a front elevational view of a third embodiment of an ultrasonic osteotome in accordance with the present invention.

FIG. 6 is a side elevational view of the ultrasonic osteotome of FIG. 5.

FIG. 7 is a front elevational view of a fourth embodiment of an ultrasonic osteotome in accordance with the present invention.

FIG. 8 is a side elevational view of the ultrasonic osteotome of FIG. 7.

FIG. 9 is a front elevational view of a fourth embodiment of an ultrasonic osteotome in accordance with the present invention.

FIG. 10 is a side elevational view of the ultrasonic osteotome of FIG. 9.

FIG. 11 is a top, front and side isometric view of the ultrasonic osteotome of FIGS. 9 and 10.

FIG. 12 is a top plan view of the ultrasonic osteotome of FIGS. 9-11.

DETAILED DESCRIPTION

FIGS. 7 and 8 depict an ultrasonic osteotome 10 comprising a shaft 12 having a distal end portion (not separately designated) with a lateral outer surface 14 and a blunt or rounded distal tip 16. A planar cutting blade 18, with a shape vaguely similar to that of a sailboat keel, is connected to the distal end portion of shaft 12 along lateral outer surface 14.

Lateral outer surface 14 and concomitantly shaft 12 extend so far on opposite sides of blade 18 as to constitute a block or stop to penetration of the shaft into an incision formed in bone tissue by the blade. More specifically, blade 18 has a pair of opposed major faces 18a and 18b and a maximum thickness t1 measured in a given direction perpendicular to major faces 18a and 18b, while shaft 12 has an effective width or breadth w1 measured substantially parallel to the given measurement direction. Width or breadth w1 of shaft 12 is sufficiently greater than thickness t1 of blade 18 so as to block or stop penetration of shaft 12 into an incision formed in bone tissue by a distal end portion of the blade. In the case of osteotome 10, the effective width or breadth w1 of lateral outer surface 14 and shaft 12 is approximately equal to the entire width of the lateral outer surface 14 on the side of shaft 12 carrying blade 18. Where the shaft has a cross-sectional shape that is a circle rather than an oblong with rounded corners, the effective width or breadth of the lateral outer surface and of the shaft may be less than the diameter of the shaft.

On a distal side, blade 18 has an edge 20 with a cutting notch 22 adjacent to lateral outer surface 14. Edge 20 also has a protruding portion or bulge 24 on a side of notch 22 opposite lateral outer surface 14. Edge 20 is continuous over or along notch 22 and bulge 24 and has an arcuate S-shaped form. In other words, blade edge 20 has no discontinuities, sudden gaps, sharp notches, sharp teeth, or other pointy features that would tend to cut, lacerate, or otherwise damage soft tissue that is disposed adjacent to bone tissue that is being cut with blade 18.

Notch 22 may be beveled, serrated or toothed. Protruding portion or bulge 24 may be beveled, serrated or toothed, but any serrations or teeth particularly along a laterally or radially outer periphery of blade 18 must be smoothly configured, without discontinuities or sharp points that would cut, lacerate, or otherwise damage soft tissue. Generally, notch 22 comes into contact only with bone tissue, while protruding portion or bulge 24, particular a most lateral part thereof, may come into contact with soft tissue underlying a target bone structure.

Blade 18 is disposed on only one side of the distal end portion of shaft 12. Shaft 12 extends in a distal direction beyond blade 18. Blade 18 is formed on a proximal side with a generally linear edge section 26 gently sloped at an acute angle 27 relative to lateral outer surface 14. It is to be noted that blade 18 may be modified to provide notch 22 and bulge 24 on a proximal side and linear edge section 26 on a distal side. Alternatively, both the distal side and the proximal side may be formed with notch and bulge, in which case there is no linear edge section 26.

Shaft 12 is depicted as having a rounded oblong configuration, with a rectangular cross-section having rounded corners. However, other shaft geometries, such as cylindrical or triangular are possible.

FIGS. 1 and 2 depict another ultrasonic osteotome 30 comprising a shaft 32 having a distal end portion (not separately enumerated) with a cylindrical lateral outer surface 34 and a blunt distal tip 36. A cutting blade 38 is connected to the distal end portion of shaft 32 both along cylindrical lateral outer surface 34 and blunt distal tip 36.

Blade 38 has a proximal blade portion 40 with a proximally facing approximately linear edge 42 sloped at an acute angle relative to lateral outer shaft surface 34. Blade 38 has a distal end portion 44 with a distally facing convex edge 46. Convex edge 46 and linear edge 42 are continuous with one another in a gently or smoothly arcuate curve having the profile of a liquid drop, skewed to one side. Blade edges 42 and 46 may be beveled or serrated, but any serrations must be smooth, without points or jagged features, to avoid soft tissue damage.

Lateral outer surface 34 extends so far on opposite sides of proximal blade portion 40 as to block or stop penetration of shaft 32 into an incision formed in bone tissue by the proximal portion of blade 38. Similarly, blunt distal tip 36 extends so far on opposite sides of distal blade portion 44 as to block or stop penetration of shaft 32 into an incision formed in bone tissue by the distal portion of blade 38. For instance, where blade 38 has a pair of opposed major faces 38a and 38b and a maximum thickness t2 measured in a given direction perpendicular to major faces 38a and 38b, blunt distal tip 36 has a width or breadth w2, measured substantially parallel to the given measurement direction, that is sufficiently greater than thickness t2 of blade 38 so as to block or stop penetration of blunt distal tip 36 into an incision formed in bone tissue by distal end portion 44 of blade 38.

Blade 38 has a width, i.e., that dimension of the blade measured between the cutting edge 42, 46 and outer surface 34, 36 of shaft 32, which varies so as to provide the user with multiple choices as to cutting depth. Thus, depending on the angle of tilt of shaft 32 relative to the surface of a target bone structure during an application of the ultrasonically vibrating osteotome 30 to the bone, blade 38 generates an incision of adjustable depth.

More specifically, proximal portion 40 of blade 38 has a maximum width d1 measured between a most laterally displaced point 48 of the blade edge and lateral outer surface 34, while distal end portion 44 of blade 38 has a maximum width d2 measured between a most distal point 49 of blade edge 46 and blunt distal tip 36. Typically, width measurements d1 and d2 are significantly different from one another and convex edge 46 provides a continuous change in blade width between point 48 and 49, thereby enabling the user to fine tune the depth of cut by controlling the angle at which shaft 32 meets the bone surface at the surgical site.

FIGS. 3 and 4 depict a further ultrasonic osteotome 50 comprising a shaft 52 having a distal end portion (not separately designated) with a cylindrical lateral outer surface 54 and a blunt distal tip 56. A cutting blade 58 is connected to blunt distal tip 36 and to lateral outer surface 54 on opposite sides of shaft 52.

Blade 58 has a first proximal blade portion 60 with a proximally facing approximately linear edge 62 sloped at an acute angle relative to lateral outer shaft surface 54 on one side of shaft 52. Blade 58 has a second proximal blade portion 60' with a proximally facing approximately linear edge 62 sloped at an acute angle relative to lateral outer shaft surface 54 on an opposite side of shaft 52. Blade 88 has a distal end portion 64 with a distally facing convex edge 66. Convex edge 66 and linear edges 62 and 62' are continuous with one another in a gently or smoothly arcuate curve having the profile of an asymmetric liquid drop. Blade edges 62, 62' and 66 may be beveled or serrated, but any serrations must be smooth, without points or jagged features, to avoid soft tissue damage.

Lateral outer surface 54 extends so far on opposite sides of proximal blade portion 60 or 60' as to block or stop penetration of shaft 52 into an incision formed in bone tissue by that proximal portion of blade 58. Similarly, blunt distal tip 56 extends so far on opposite sides of distal blade portion 64 as to block or stop penetration of shaft 52 into an incision formed in bone tissue by the distal portion of blade 58. For instance, where blade 58 has a pair of opposed major faces 58a and 58b and a maximum thickness t3 measured in a given direction perpendicular to major faces 58a and 58b, blunt distal tip 56 has a width or breadth w3, measured substantially parallel to the given measurement direction, that is sufficiently greater than thickness t3 of blade 58 so as to block or stop penetration of blunt distal tip 56 into an incision formed in bone tissue by distal end portion 64 of blade 58.

Blade 58 has a width dimension, measured between the continuous cutting edge 62, 66, 62' and the outer surface 54, 56 of shaft 52, which varies so as to provide the user with multiple choices as to cutting depth. Accordingly, blade 58 is utilizable to generate +an incision of a depth that depends on the angle of tilt of shaft 52 relative to the surface of a target bone structure during an application of the ultrasonically vibrating osteotome 50 to the bone.

First proximal portion 60 of blade 58 has a maximum width d1' measured between (i) a most laterally displaced point 68 of the blade edge on one side of shaft 52 and (ii) lateral outer surface 54. Second proximal blade portion 60' has a maximum width d3' measured between (i) a most laterally displaced point 68' of the blade edge on another side of shaft 52 and (ii) lateral outer surface 54. Distal end portion 64 of blade 58 has a maximum width d2' measured between a most distal point 69 of convex blade edge 66 and blunt distal tip 56. Typically, width measurements d1', d2', d3' are significantly different from one another and convex edge 66 provides a continuous change in blade width between points 68, 68' on the one hand and point 69 on the other hand, thereby enabling the user to fine tune the depth of cut by controlling the angle at which shaft 52 meets the bone surface at the surgical site.

FIGS. 5 and 6 depict yet another ultrasonic osteotome 70 comprising a shaft 72 having a distal end portion (not separately enumerated) with a cylindrical lateral outer surface 74 and a blunt distal tip 76. A cutting blade 78 is connected to the distal end portion of shaft 72 only along cylindrical lateral outer surface 74. Blade 78 is disposed in greatest part only along one side of shaft 72. Lateral outer surface 74 and blunt distal tip 76 extend so far on opposite sides of blade 78 as to block or stop penetration of shaft 72 into an incision formed in bone tissue by the blade.

Blade 78 has a proximal blade portion 80 with a proximally facing approximately linear edge 82 sloped at an acute angle relative to lateral outer shaft surface 74. Blade 78 has a distal end portion 84 with a distally facing convex edge 86. Distal end portion 84 is disposed distally of, and nearly entirely laterally of, blunt distal tip 76. Convex edge 86 and linear edge 82 are continuous with one another in a gently or smoothly arcuate curve having the profile of a liquid drop, skewed to one side. Blade edges 82 and 86 may be beveled or serrated, but any serrations must be smooth, without points or jagged features, to avoid soft tissue damage.

Lateral outer surface 74 extends so far on opposite sides of proximal blade portion 80 as to block or stop penetration of shaft 72 into an incision formed in bone tissue by the proximal portion of blade 78. Similarly, blunt distal tip 76 extends so far on opposite sides of distal blade portion 84 as to block or stop penetration of shaft 72 into an incision formed in bone tissue by the distal portion of blade 78. For instance, where blade 78 has a pair of opposed major faces 78a and 78b and a maximum thickness t4 measured in a given direction perpendicular to major faces 78a and 78b, blunt distal tip 76 has a width or breadth w4, measured substantially parallel to the given measurement direction, that is sufficiently greater than thickness t4 of blade 78 so as to block or stop penetration of blunt distal tip 76 into an incision formed in bone tissue by distal end portion 84 of blade 78.

Blade 78 has a width, i.e., that dimension of the blade measured between the cutting edge 82, 86 and outer surface 74, 76 of shaft 72, which varies so as to provide the user with multiple choices as to cutting depth. Thus, depending on the angle of tilt of shaft 72 relative to the surface of a target bone structure during an application of the ultrasonically vibrating osteotome 70 to the bone, blade 78 generates an incision of adjustable depth.

More specifically, proximal portion 80 of blade 78 has a maximum width d1" measured between a most laterally displaced point 88 of the blade edge and lateral outer surface 74, while distal end portion 84 of blade 78 has a maximum width d2" measured between a most distal point 89 of blade edge 86 and blunt distal tip 76. Typically, width measurements d1" and d2" are significantly different from one another and convex edge 86 provides a continuous change in blade width between point 88 and 89, thereby enabling the user to fine tune the depth of cut by controlling the angle at which shaft 72 meets the bone surface at the surgical site.

Blades 18, 38, 58, and 78 are centrally disposed relative to the respective shafts 12, 32, 52, and 72, so that the blades each lie in a common plane with an axis of symmetry of the distal end portion of the respective shaft. Thus, blades 18, 38, 58, and 78 are disposed in planes oriented substantially perpendicularly to lateral outer surfaces 14, 34, 54, and 74. Alternatively, it is possible for blades 18, 38, 58, and 78 to be eccentrically disposed, i.e., disposed in planes that are not coaxial with the distal end portions of the respective shafts 12, 32, 52, and 72, but extend parallel with the respective axis of symmetry. In this alternative configuration, blunt distal tips 36, 56, and 76 extend eccentrically on laterally or transversely opposite sides of distal end portions 44, 64, and 84 of blades 32, 52, and 72, respectively.

Shafts 12, 32, 52, and 72 and the respective lateral outer surfaces 14, 34, 54, and 74 may be curved to match curvatures of outer bone surfaces, as indicated at 90, 92, 94, and 96. In that case, lateral outer surfaces 14, 34, 54, and 74 each have an arcuate profile in a longitudinal plane including an axis of the respective shaft 12, 32, 52, and 72.

An ultrasonic osteotome in accordance with the present invention facilitates bone cutting by preventing the blade from extending through a target bone tissue mass at a surgical site and substantially into soft tissue underlying the target bone. Thus, the ultrasonic osteotome described herein protects soft tissue while enabling a smooth clean incision through overlying bone.

Generally, that portion of lateral outer surface 14, 34, 54, 74 or of blunt distal tip 36, 56, 76 that comes into contact with the target tissue of the patient at a surgical site has a total effective width, measured perpendicularly to the respective blade 18, 38, 58, 78, which is at least two times the thickness of the blade. More preferably, the tissue-contacting portion of the lateral outer surface 14, 34, 54, 74 or of blunt distal tip 36, 56, 76 has a width that is about three times the thickness of the respective blade 18, 38, 58, 78. It is contemplated that blades 18, 38, 58, 78 are thin flat plates, with thicknesses on the order of 0.0020 inch. Consequently, the tissue-contacting portion of the lateral outer surface 14, 34, 54, 74 or of blunt distal tip 36, 56, 76 has a width that is at least about 0.0040 to 0.0060 inch wide.

In the case of shafts 32, 52, and 72 which are cylindrical at their distal ends, the widths of the tissue-contacting portion of the lateral outer surface 14, 34, 54, 74 is a fraction of the shaft diameter, typically between one-third and two-thirds.

Blades 18, 38, 58, and 78 provide incision depths generally between 4 and 10 mm.

FIGS. 9-12 depict an ultrasonic osteotome 110 comprising a shaft 112 having a distal end portion (not separately designated) with a lateral outer surface 114 and a blunt or rounded distal tip 116. A serrated planar cutting blade 118, with a shape vaguely similar to that of a fish fin, is connected to the distal end portion of shaft 112 along lateral outer surface 114.

Lateral outer surface 114 and concomitantly shaft 112 extend so far on opposite sides of blade 118 as to constitute a block or stop to penetration of the shaft into an incision formed in bone tissue by the blade. More specifically, blade 118 has a pair of opposed major faces 118a and 118b and a maximum thickness t1' measured in a given direction perpendicular to major faces 118a and 118b, while shaft 112 has an effective width or breadth w1' measured substantially parallel to the given measurement direction. Width or breadth w1' of shaft 112 is sufficiently greater than thickness t1' of blade 118 so as to block or stop penetration of shaft 112 into an incision formed in bone tissue by the blade. In the case of osteotome 110, the effective width or breadth w1' of lateral outer surface 114 and shaft 12 is generally between one-third and one-half the radius of shaft 112 (which is cylindrical except for distal tip 116). Thus, lateral surface 114 is a portion of the entire cylindrical outer surface of shaft 112, that portion being located on the side of shaft 112 carrying blade 118.

Blade 118 has a cutting edge 120 with an inner or notch section 122 adjacent and inclined with respect to lateral outer surface 114. Edge 120 also has a protruding portion or bulge 124 on the distal or forward facing side. Blade 118 is disposed on only one side of the distal end portion of shaft 112. Shaft 112 extends in a distal direction beyond blade 18: distal tip 116 is located distally of bulge 124. Blade 118 is formed on a proximal and outer side with a generally linear edge section 126 gently sloped at an acute angle relative to lateral outer surface 114.

Inner edge or notch section 122, edge bulge 124 and outer edge section 126 are formed with serrations or teeth 128. Serrations or teeth 128' along an outer aspect of bulge 124 (at least) are smoothly configured, without discontinuities or sharp points that would cut, lacerate, or otherwise damage soft tissue.

Shafts 112 and lateral outer surface 114 may be curved to match curvatures of outer bone surfaces, as discussed above with reference to bone curves 90, 92, 94, and 96.

Although the invention has been described in terms of particular embodiments and applications, one of ordinary skill in the art, in light of this teaching, can generate additional embodiments and modifications without departing from the spirit of or exceeding the scope of the claimed invention. For example, while the blades shown in the drawings are primarily designed for cutting bone tissue under a distally applied (pushing) force, it is possible to rearrange the orientation of the blades on the shafts so that cutting occurs mainly under a proximally applied (pulling) force. Pursuant to such a modification, in the embodiment of FIGS. 7 and 8, notch 22 and bulge 24 would face in the proximal direction rather than the depicted distal direction. Similarly, in the embodiment of FIGS. 9-12, blade 118 could be reversed 180° in its orientation. Accordingly, it is to be understood that the drawings and descriptions herein are proffered by way of example to facilitate comprehension of the invention and should not be construed to limit the scope thereof.

What is claimed is:

1. An ultrasonic osteotome comprising:
   a shaft having a distal end portion with a lateral outer surface; and
   a planar or flat cutting blade connected to said distal end portion of said shaft at least in part at said lateral outer surface, at least a portion of said blade extending a longitudinally along said distal end portion of said shaft and being disposed laterally on one side thereof so that a portion of said shaft is distal to at least part of said blade,
   said lateral outer surface extending so far on opposite sides of said blade as to block or stop penetration of said shaft into an incision formed in bone tissue by said blade wherein said blade has an edge formed on at least one side with a notch adjacent to said lateral outer surface and a protruding bulge on a side of said notch opposite said lateral outer surface, said shaft extending in a distal direction beyond said notch, thereby serving to define said notch along one side thereof.

2. The osteotome defined in claim 1 wherein said edge is continuous over said notch and said bulge and has an arcuate form.

3. The osteotome defined in claim 2 wherein said edge along said notch and said bulge has an S-shaped configuration.

4. The osteotome defined in claim 1 wherein said notch and said bulge are disposed on a distal side of said blade and face in a distal direction.

5. The osteotome defined in claim 1 wherein said notch or said edge is serrated.

6. The osteotome defined in claim 1 wherein said bulge or said edge is serrated.

7. The osteotome defined in claim 1 wherein said shaft extends in a distal direction beyond said blade.

8. The osteotome defined in claim 1 wherein said edge of said blade is sloped, on a proximally facing side, at an acute angle relative to said lateral outer surface.

9. The osteotome defined in claim 1 wherein said shaft and said lateral outer surface are curved so as to have an arcuate profile in a longitudinal plane including an axis of said shaft.

10. The osteotome defined in claim 1 wherein said distal end portion of said shaft has a longitudinal axis, said blade being coplanar with said axis.

11. The osteotome defined in claim 1 wherein said lateral outer surface includes a portion at said blade that is planar.

12. The osteotome defined in claim 1 wherein said blade is disposed in a plane oriented perpendicularly to said lateral outer surface.

13. The osteotome defined in claim 1 wherein said blade is disposed in a plane extending parallel to an axis of a distal end portion of said shaft.

14. The osteotome defined in claim 1 wherein said lateral outer surface extends longitudinally along said blade and contiguously therewith on said opposite sides of said blade as to block or stop penetration of said shaft into an incision formed in bone tissue by said blade.

* * * * *